(12) United States Patent
Fritsch et al.

(10) Patent No.: US 6,588,042 B2
(45) Date of Patent: *Jul. 8, 2003

(54) BRUSH SECTION FOR AN ELECTRIC TOOTHBRUSH

(75) Inventors: Thomas Fritsch, Eppstein (DE); Hansjörg Reick, Kronberg (DE)

(73) Assignee: Bruan GmbH, Kronberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/002,827

(22) Filed: Nov. 15, 2001

(65) Prior Publication Data

US 2002/0035761 A1 Mar. 28, 2002

Related U.S. Application Data

(63) Continuation of application No. 09/506,152, filed on Feb. 17, 2000, which is a continuation of application No. PCT/EP98/04750, filed on Jul. 30, 1998.

(30) Foreign Application Priority Data

Oct. 17, 1997 (DE) .......................... 197 45 876

(51) Int. Cl.⁷ .......................... A61C 17/34; A46B 13/02
(52) U.S. Cl. .......................... 15/22.1; 15/28; 403/313; 403/314; 403/326; 403/377
(58) Field of Search .......................... 15/28, 22.1, 22.2, 15/22.3, 22.4, 23, 29, 24; 403/313, 314, 326, 374, 377

(56) References Cited

U.S. PATENT DOCUMENTS

| 3,183,538 | A |   | 5/1965  | Hibner       | 15/22  |
|-----------|---|---|---------|--------------|--------|
| 3,195,537 | A |   | 7/1965  | Blasi        | 128/56 |
| 3,220,039 | A |   | 11/1965 | Dayton et al.| 15/28  |
| 3,939,599 | A |   | 2/1976  | Henry et al. | 32/59  |
| 4,156,620 | A |   | 5/1979  | Clemens      | 134/6  |
| 4,827,550 | A |   | 5/1989  | Graham et al.| 15/22  |
| 4,827,552 | A |   | 5/1989  | Bojar et al. | 15/28  |
| 4,989,287 | A |   | 2/1991  | Scherer      | 15/22.1|
| 5,054,149 | A |   | 10/1991 | Si-Hoe et al.| 15/28  |
| 5,289,604 | A |   | 3/1994  | Kressner     | 15/22.1|
| 5,359,747 | A |   | 11/1994 | Amakasu      | 15/22.1|
| 5,435,032 | A | * | 7/1995  | McDougall    | 15/22.1|
| 5,461,744 | A |   | 10/1995 | Merbach      | 15/22.1|
| 5,625,916 | A |   | 5/1997  | McDougall    | 15/28  |
| 6,308,359 | B2|   | 10/2001 | Fritsch et al.| 15/28 |

FOREIGN PATENT DOCUMENTS

| CH | 368 780    | 6/1963 |       |
|----|------------|--------|-------|
| DE | 1 212 036  | 3/1966 |       |
| FR | 1 299 056  | 6/1962 |       |
| GB | 477799     | 1/1938 | 15/28 |
| JP | 53-21650   | 2/1978 |       |
| WO | WO91/07117 | 5/1991 |       |

OTHER PUBLICATIONS

Color photographs of Bausch & Lomb "Interplak" Model PB–4B style Handpiece with travel protection switch and Toothbrush attachment (handpiece stamped "1D IA", believed circa 1992 on sale in the United States) (7 views). Package rear and bottom panels of Bausch & Lomb Interplak Model PB–4B, marked © 1990 (color copy, 1 sheet).

(List continued on next page.)

*Primary Examiner*—Gary K. Graham
(74) *Attorney, Agent, or Firm*—Edward S. Podszus

(57) ABSTRACT

The invention is directed to a brush section (2) for an electric toothbrush (1), having a carrier tube (4) to which is fitted a bristle carrier (5) comprising a plurality of bristles (6). The carrier tube (4) is adapted to plug onto a mount (7) of a hand piece (3) of the electric toothbrush (1). Provision is made for spring elements (14) arranged between the carrier tube (4) and the mount (7). Noises and vibrations are thereby reduced when the electric toothbrush (1) is in the activated condition.

124 Claims, 2 Drawing Sheets

OTHER PUBLICATIONS

Product use instructions to Bausch & Lomb Interplak travel–style "Voyager" model TK–2 marked © 1991 (6 photocopied sheets containing cover and pp. 1–10).

Color photographs of Bausch & Lomb "Interplak" Model PB–6 style Handpiece with waterproof electronic travel protection switch (believed circa 1992 on sale in the United States) (6 views).

Package rear and bottom panels of Bausch & Lomb Interplak Model PB–6, marked © 1992 (color copy, 1 sheet).

* cited by examiner

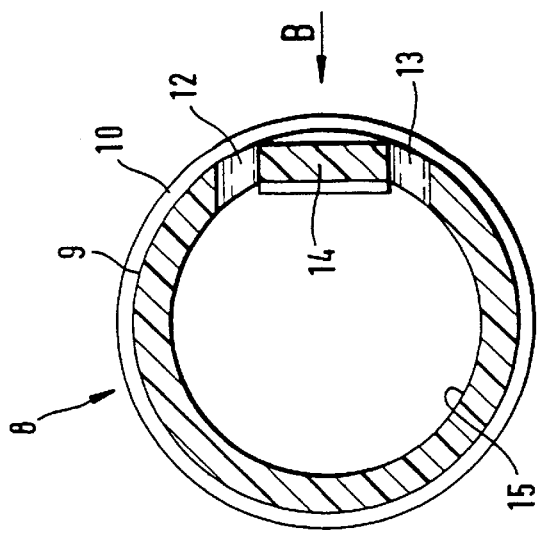
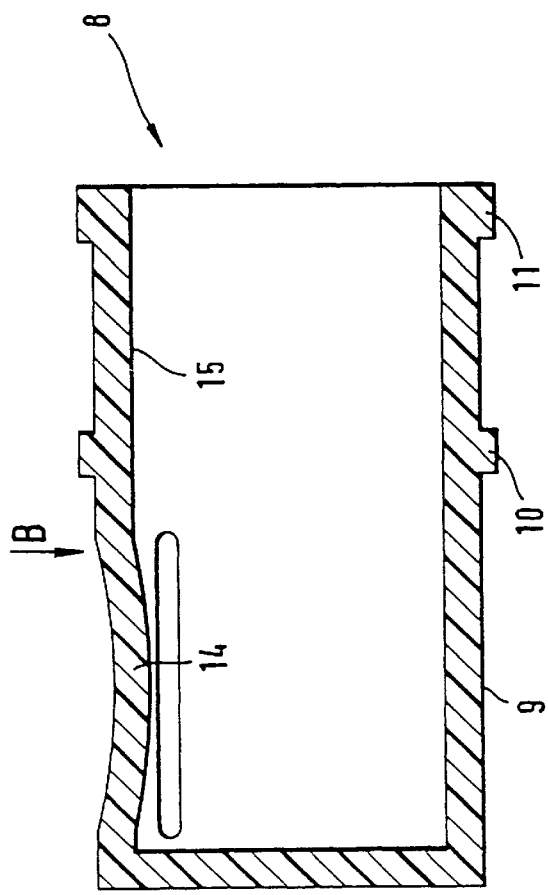
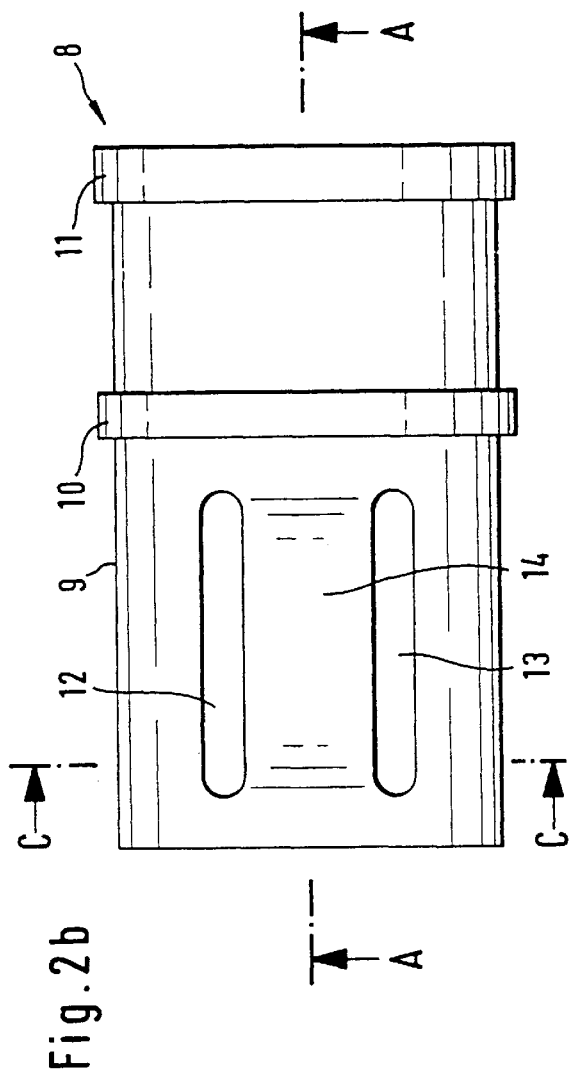

BRUSH SECTION FOR AN ELECTRIC TOOTHBRUSH

This application is a continuation of application U.S. Ser. No. 09/506,152, filed on Feb. 17, 2000, now allowed, which is a continuation application of International Application PCT/EP98/04750, with an international filing date of Jul. 30, 1998.

This invention relates to a brush section for an electric toothbrush, having a carrier tube to which is fitted a bristle carrier comprising a plurality of bristles, and being adapted to plug onto a mount of a hand piece of the electric toothbrush. Further, the present invention relates to an electric toothbrush with a hand piece and a brush section of the aforementioned type.

A brush section of this type and an electric toothbrush of this type are generally known and commercially available.

An electric motor and a storage battery are accommodated in the hand piece of the electric toothbrush. The bristle carrier held on the brush section is mounted on the carrier tube for rotary or pivotal motion. When the toothbrush is activated, a rotary motion produced by the electric motor is transmitted to the bristle carrier by way of suitable shafts and joints. Hence the bristles are made to perform a cleaning movement. The bristles can be placed by a user against the surface of his teeth and thus used for dental care.

In the course of time the bristles of the brush section become worn and have to be replaced. It is partly for this reason that the brush section is designed to be plugged on the hand piece because then it can be replaced. The carrier tube of the brush section and the mount of the hand piece are coordinated to be joinable together by positive engagement. In this manner the brush section is fixedly held on the hand piece in a positive-engagement relationship thereto.

Plugging on the brush section and, in particular, pulling it off the hand piece should not require too much force of the user. This is why, as previously mentioned, provision is only made for a positive-engagement relationship between the carrier tube and the mount. A press-fit connection or the like is not possible. Consequently, the carrier tube and the mount usually display a certain play.

When the electric toothbrush is activated this play results in a movement which is oriented particularly in a radial direction but also partly in a tangential direction. This movement creates undesirable noises and vibrations of the brush section relative to the hand piece. Furthermore, said movement makes it at least more difficult for optimum transmission of the cleaning movement to the surface of the teeth.

SUMMARY OF THE INVENTION

It is an object of the present invention to devise a brush section for an electric toothbrush such that it enables a zero-play connection with the hand piece yet does not require greater force of the user when plugging on or pulling off the brush section.

This object is accomplished with a brush section of the type initially referred to by providing spring elements arranged between the carrier tube and the mount.

The spring elements ensure that the carrier tube and hence the brush section adopts a zero-play position on the mount and hence on the hand piece. Undesirable movements of the brush section in the activated state are thus reliably prevented, as are the noises and vibrations resulting therefrom. At the same time the spring elements require no special force of the user when plugging the brush section on the hand piece. On account of the resilient characteristics of the spring elements the user has to overcome only a small resistance in order to urge back the spring elements and plug the carrier tube on the mount. Overcoming this resistance signifies no great effort and hence no reduction of comfort for the user but is taken rather as a sign that the brush section is now plugged correctly on the hand piece. Thanks to the spring elements the brush section is fixedly held on the mount of the hand piece in such a way that no relative movements arise between the profiled sleeve and the mount when the brush head is pressed (or better placed) against the surface of the teeth and when only small contact forces are applied. It is thereby ensured that even smallest movements of the mount are invariably transmitted to the mouthpiece.

In an advantageous further aspect of the present invention the spring elements are either fitted to the brush section or are fitted to the hand piece and/or the mount and/or are adapted to plug onto the mount. The spring elements can thus be assigned to the component best suited for design reasons for implementation of the same. This may be not only the brush section but also the hand piece and particularly its mount. Similarly, it is possible to design the spring elements as a separate component to be plugged on the hand piece and/or the mount.

If the spring elements are assigned to the brush section, provision is made in a first advantageous embodiment of the invention for a sleeve equipped with the spring elements and adapted to plug into the carrier tube. Hence with a view to the material selection, for example, the spring elements can be manufactured independently of the other components of the brush section. Similarly, the spring elements can be constructed with an optimum design for their intended function, without having to make allowance for any particular fringe conditions of the brush section's other components.

If the spring elements are assigned to the brush section, provision is made in a second advantageous embodiment of the invention for the carrier tube to be equipped with the spring elements. No separate component is needed, therefore, to implement the spring elements. Instead the spring elements are integrated in the carrier tube. This represents a particularly simple and convenient way to accommodate the spring elements, particularly with a view to the material outlay and production effort required.

In an advantageous further aspect of the present invention, the sleeve or the carrier tube includes as spring elements at least one shoulder having a bend that curves in the direction of the mount. The spring elements are thus implemented by means of one or several curved shoulders. This shoulder ultimately forms a type of bending bar whose curvature results in the desired resilient characteristics. Starting from the sleeve plugged onto the carrier tube or from the carrier tube the curve is oriented in the direction of the hand piece mount. When the mount is inserted in the carrier tube, the curve is oriented inwards. A certain resistance develops on the curve of the shoulder which the user is in a position to overcome using a slight pressing motion. The resilient characteristics of the shoulder then act on the brush section in such a way that it is held in the mount without play.

Particularly conveniently, the sleeve or the carrier tube is made of a plastics material. The shoulder is thus also made of plastic so that the plastic's capability of being bent has an advantageous effect on the resilient properties of the shoulder.

Further features, application possibilities and advantages of the present invention will become apparent from the subsequent description of embodiments of the invention illustrated in the Figures of the accompanying drawing. It will be understood that any single feature and any combination of single features described or represented by illustration form the subject-matter of the present invention, irrespective of their summary in the patent claims or their back reference, as well as irrespective of their wording and representation in the description and the drawing, respectively. In the drawing,

BRIEF DESCRIPTION OF THE DRAWINGS

FIGS. 2a to 2c represent schematically a longitudinal sectional view, a top plan view and a cross-sectional view, respectively, of a sleeve of the brush section of FIG. 1.

DETAILED DESCRIPTION OF PREFERRED EMBODIMENTS

Figure 1:
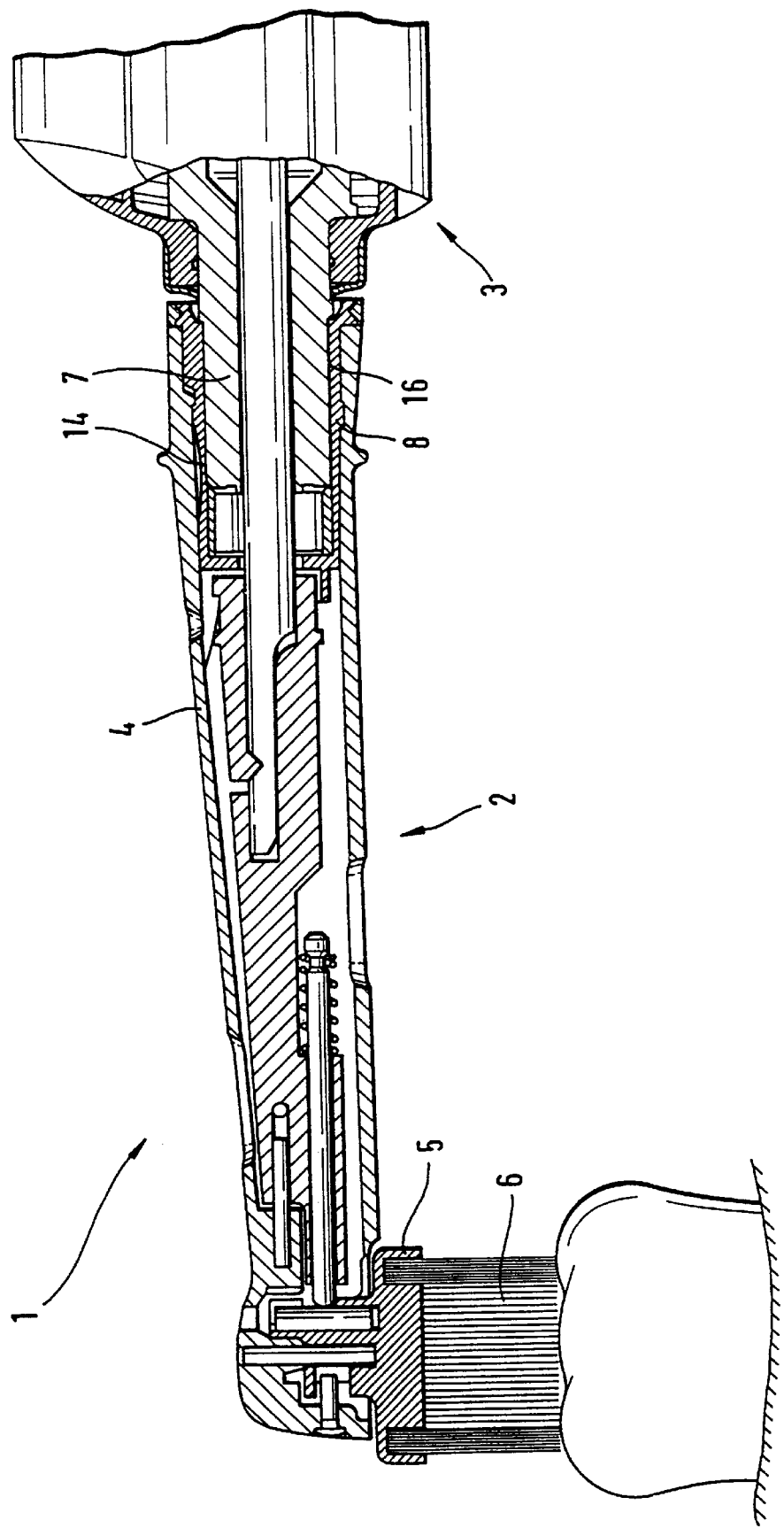
FIG. 1 is a schematic longitudinal sectional view of a brush section for an electric toothbrush illustrating an embodiment of the present invention.

FIG. 1 shows an electric toothbrush 1 having a brush section 2 and a hand piece 3. The brush section 2 is plugged on the hand piece 3 but can be pulled off the hand piece 3 in order, for example, to be replaced by a different brush section 2.

The brush section 2 has an elongate carrier tube 4 with a bristle carrier 5 projecting at approximately right angles from the tube end remote from the hand piece 3. The bristle carrier 5 is equipped with a plurality of bristles 6. At its end close to the brush section 2 the hand piece 3 has a mount 7 on which the brush section 2 is plugged.

Further accommodated in the hand piece 3 are an electric motor and a storage battery. With the electric toothbrush 1 activated, a rotary or pivotal motion produced by the electric motor is transmitted by means of shafts, couplings, gears and the like to the bristle carrier 5 which thus performs a rotary or pivotal motion about an axis approximately parallel to the bristles 6.

With the electric toothbrush 1 actuated, a user can place the bristles 6 against the surfaces of his teeth and use the rotary or pivotal motion of the bristle carrier 5 to clean and care for his teeth.

A sleeve 8 is provided in the end of the brush section 2 close to the hand piece 3. In this area of the brush section 2 the carrier tube 4 is of an approximately cylindrical configuration and the sleeve 8 is plugged in the carrier tube 4. The sleeve 8 is secured against rotary movement in the carrier tube 4 as by ridges or the like engaging in grooves. Furthermore, the sleeve 8 is secured against being pulled out of the carrier tube 4 by detent elements or the like.

FIGS. 2a to 2c show the sleeve 8 of the brush section 2 on an enlarged scale.

The sleeve 8 is of a cylindrical construction and has an essentially circular cross section. On its outside wall 9 the sleeve 8 has two circumferential annular ridges 10, 11, at least one of which can act as detent element.

In the longitudinal direction the sleeve 8 has two slots 12, 13, with a shoulder 14 constructed in between. As can be seen in FIG. 2a in particular, the shoulder 14 is equipped with a curve or bend. The latter is oriented inwards, meaning toward the smaller diameters, and hence in the direction of the mount 7 of the hand piece 3.

At least the shoulder 14 is made of a flexible or elastic material. The entire sleeve 8 in particular is made of a plastics material. The shoulder 14 thus forms a bending bar with resilient properties. Hence the shoulder 14 performs the function of spring elements.

The inside wall 15 of the sleeve 8 has a cross-sectional shape and a diameter conforming to the outside wall 16 of the mount 7 so that the mount 7 can be plugged in the sleeve 4 by positive engagement therewith. Where applicable, the sleeve 8 and the mount 7 have cross sectional shapes designed to permit the sleeve 8 and hence the brush section 2 to be plugged on the mount 7 and hence on the hand piece 3 only when turned to a certain position.

To plug the brush section 2 on the hand piece 3, the mount 7 of the hand piece 3 has to be inserted in the sleeve 8 of the brush section 2. As this occurs, the sleeve 8 is itself plugged in the carrier tube 4 of the brush section 2. When the mount 7 reaches the inward projecting bend of the shoulder 14, a certain resistance results. This resistance is overcome by pressing back the bend of the shoulder 14. The mount 6 can then be inserted fully in the sleeve 8. The brush section 2 is thus plugged fully on the hand piece 3.

In a configuration differing from the sleeve 8 as described, there can be either two or more shoulders 14 and 14". The shoulder or shoulders 14 do not have to be fastened at both ends (see 14'); it is also possible for the shoulder or shoulders 14 to be fixed at one end only (14'). The slots 12, 13 defining the shoulder or shoulders 14 may also be implemented by reductions in wall thickness (12', 13') to the sleeve 8 so that the sleeve is completely closed around its circumference. It is also possible for the spring elements to be incorporated generally in the sleeve 8 as elastic components in the broadest sense.

It is likewise possible for the spring elements to be arranged directly on the carrier tube 4, thereby eliminating the need for the sleeve 8. This can be accomplished, for example, by providing the shoulder or shoulders 14 directly on the carrier tube 4. At least the shoulder or shoulders 14, or the complete carrier tube 4 as well, are then made particularly of a plastics material, thus producing the desired resilient characteristics.

Another possibility is for the spring elements to be assigned to the hand piece 3 and not to the brush section 2. In this arrangement the spring elements can be provided directly on the hand piece 3 or on the mount 7. Similarly it is possible for the spring elements, for example, in the form of a sleeve or the like, to be plugged on the mount 7.

Further, the spring elements can be constructed so that they produce not only a force outwards in a radial direction but also a force in a tangential direction. This enables tangential movements of the brush section in the activated state to be prevented and vibrations and noises to be further reduced.

We claim:

1. A brush section for an electric toothbrush hand piece having a drive shaft and a mount, the mount being not rigidly connected to the drive shaft, said brush section comprising a carrier tube having a major longitudinal axis to which is fitted a bristle carrier comprising a plurality of bristles, said carrier tube being adapted to plug onto the mount of the hand piece of the electric toothbrush, said bristle carrier being movable relative the carrier tube, wherein at least one elongate shoulder made of a plastics material forms a spring element arranged between the carrier tube and the mount, said elongate shoulder being attached to the brush section and disposed on an inwardly directed surface of the carrier tube and having, along a length of said elongate shoulder, an average height in a radially inward direction protruding inwards from the adjacent inwardly directed tube surface, and wherein the elongate shoulder's length along the longitudinal axis is substantially greater than its average height so as to define a distributed abutment surface area for contacting the mount.

2. The brush section of claim 1 in combination with an electric toothbrush hand piece.

3. The brush section of claim 1, wherein the spring element is deflectable relative the carrier tube upon plugging the brush section onto the mount.

4. The brush section of claim 1, wherein the carrier tube is adapted to surround the mount in a radial direction.

5. The brush section of claim 1, wherein the at least one elongate shoulder comprises at least two elongate shoulders disposed on respective radially inwardly directed surfaces.

6. The brush section of claim 1, wherein the elongate shoulder plastics material comprises an elastic material.

7. A brush section for an electric toothbrush hand piece having a drive shaft and a mount, the mount being not rigidly connected to the drive shaft, said brush section comprising
   a carrier tube having a major longitudinal axis to which is fitted a bristle carrier comprising a plurality of bristles, said carrier tube being adapted to plug onto the mount of the hand piece of the electric toothbrush,
   wherein at least one elongate shoulder made of a plastics material forms a spring element arranged between the carrier tube and the mount,
   said elongate shoulder being attached to the brush section and disposed on an inwardly directed surface of the carrier tube and having, along a length of said elongate shoulder, an average height in a radially inward direction protruding inwards from the adjacent inwardly directed tube surface, and wherein the elongate shoulder's length along the longitudinal axis is substantially greater than its average height so as to define a distributed abutment surface area for contacting the mount, and
   further comprising a sleeve on which is disposed the spring element, said sleeve being adapted to plug into the carrier tube.

8. The brush section of claim 7, wherein the elongate shoulder is molded with the sleeve.

9. A brush section for an electric toothbrush hand piece having a drive shaft and a mount, the mount being not rigidly connected to the drive shaft, said brush section comprising
   a carrier tube having a major longitudinal axis to which is fitted a bristle carrier comprising a plurality of bristles, said carrier tube being adapted to plug onto the mount of the hand piece of the electric toothbrush,
   wherein at least one elongate shoulder made of a plastics material forms a spring element arranged between the carrier tube and the mount,
   said elongate shoulder being attached to the brush section and disposed on an inwardly directed surface of the carrier tube and having, along a length of said elongate shoulder, an average height in a radially inward direction protruding inwards from the adjacent inwardly directed tube surface, and wherein the elongate shoulder's length along the longitudinal axis is substantially greater than its average height so as to define a distributed abutment surface area for contacting the mount, and
   wherein the elongate shoulder is configured as a sleeve received within the carrier tube.

10. A brush section for an electric toothbrush having an output drive shaft and a hand piece, said hand piece having a mount for receiving said brush section, said mount extending from the hand piece along an extension axis, and said output drive shaft being moveable with respect to said mount, said brush section comprising
    a carrier tube to which is fitted a bristle carrier comprising a plurality of bristles, said bristle carrier being movable relative the carrier tube, and further comprising a longitudinal axle movably disposed within the carrier tube and drivingly connected to the bristle carrier and adapted to be coupled to the hand piece output drive shaft,
    said carrier tube having a base region adapted to be removably and fixedly attached to the mount of the toothbrush hand piece by movement of said carrier tube along a tube connection axis toward said mount,
    said base region having inwardly directed side surfaces for mating with outwardly directed surfaces of said mount,
    said base region having a mount-receiving recess partially defined by said inwardly directed surfaces and longitudinally extending along said tube connection axis,
    said base region including a resilient latch member disposed on a portion of said inwardly directed side surfaces and projecting into the recess and partially occluding entry therein of the mount,
    said latch member being deflectable relative said carrier tube by movement of said mount into said recess translationally along its extension axis aligned with the tube connection axis so as to bias the latch member between said carrier tube and said mount in contacting relationship with said outwardly directed surfaces of said mount to frictionally engage said brush section on said mount.

11. The brush section of claim 10, wherein said recess has an entrance, and said latch has latch camming structure facing the entrance and that is shaped and positioned to interact with corresponding mount structure to facilitate deflection of said latch.

12. The brush section of claim 10, wherein the latch is constructed as a cantilever beam.

13. The brush section of claim 10, wherein the latch member is more resilient than the carrier tube.

14. The brush section of claim 10, wherein, as seen in a plane transverse to the tube connection axis, the inwardly directed surfaces of the brush section define a shape which is not rotationally symmetric about the tube connection axis, and the inwardly directed surfaces of the brush section cooperate with the outwardly directed surfaces of the mount to attach said brush section to said mount at the predetermined orientation.

15. The brush section of claim 10, wherein the latch member is disposed on the carrier tube.

16. The brush section of claim 10 in combination with an electric toothbrush hand piece.

17. The brush section of claim 10, wherein the carrier tube is adapted to surround the mount in a radial direction.

18. The brush section of claim 10 wherein the base region has at least two said latch members disposed on respective inwardly directed surfaces.

19. The brush section of claim 18, wherein the latch member comprises an elastic material.

20. A brush section for an electric toothbrush having an output drive shaft and a hand piece, said hand piece having a mount for receiving said brush section, said mount extending from the hand piece along an extension axis, and said output drive shaft being moveable with respect to said mount, said brush section comprising a carrier tube to which is fitted a bristle carrier comprising a plurality of bristles, said carrier tube having a base region adapted to be removably and fixedly attached to the mount of the toothbrush hand piece by movement of said carrier tube along a tube connection axis toward said mount, said base region having inwardly directed side surfaces for mating with outwardly directed surfaces of said mount, said base region having a mount-receiving recess partially defined by said inwardly directed surfaces and longitudinally extending along said tube connection axis, said base region including a resilient latch member disposed on a portion of said inwardly directed side surfaces and projecting into the recess and partially occluding entry therein of the mount, said latch member being deflectable relative said carrier tube by movement of said mount into said recess translationally along its extension axis aligned with the tube connection axis so as to bias the latch member between said carrier tube and said mount in contacting relationship with said outwardly directed surfaces of said mount to frictionally engage said brush section on said mount, and wherein the bristle carrier is rotatable relative the carrier tube, and further comprising a longitudinal axle rotationally disposed within the carrier tube and drivingly connected to the bristle carrier and adapted to be coupled to the hand piece output drive shaft during the translational movement of the mount into the recess along the connection axis.

21. A brush section for an electric toothbrush having an output drive shaft and a hand piece, said hand piece having a mount for receiving said brush section, said mount extending from the hand piece along an extension axis, and said output drive shaft being moveable with respect to said mount, said brush section comprising a carrier tube to which is fitted a bristle carrier comprising a plurality of bristles, said carrier tube having a base region adapted to be removably and fixedly attached to the mount of the toothbrush hand piece by movement of said carrier tube along a tube connection axis toward said mount, said base region having inwardly directed side surfaces for mating with outwardly directed surfaces of said mount, said base region having a mount-receiving recess partially defined by said inwardly directed surfaces and longitudinally extending along said tube connection axis, said base region including a resilient latch member disposed on a portion of said inwardly directed side surfaces and projecting into the recess and partially occluding entry therein of the mount, said latch member being deflectable relative said carrier tube by movement of said mount into said recess translationally along its extension axis aligned with the tube connection axis so as to bias the latch member between said carrier tube and said mount in contacting relationship with said outwardly directed surfaces of said mount to frictionally engage said brush section on said mount, and further comprising a sleeve on which is disposed the latch member, said sleeve being adapted to plug into the carrier tube.

22. The brush section of claim 21, wherein the elongate shoulder is molded with the sleeve.

23. The brush section of claim 21, wherein at least one of the sleeve and the carrier tube comprises at least one shoulder forming said latch member, said at least one shoulder having a bend that curves in the direction of the mount.

24. The brush section of claim 21, wherein at least one of the sleeve and the carrier tube is made of a plastics material.

25. A brush section for an electric toothbrush having an output drive shaft and a hand piece, said hand piece having a mount for receiving said brush section, said mount extending from the hand piece along an extension axis, and said output drive shaft being moveable with respect to said mount, said brush section comprising a carrier tube to which is fitted a bristle carrier comprising a plurality of bristles, said carrier tube having a base region adapted to be removably and fixedly attached to the mount of the toothbrush hand piece by movement of said carrier tube along a tube connection axis toward said mount, said base region having inwardly directed side surfaces for mating with outwardly directed surfaces of said mount, said base region having a mount-receiving recess partially defined by said inwardly directed surfaces and longitudinally extending along said tube connection axis, said base region including a resilient latch member disposed on a portion of said inwardly directed side surfaces and projecting into the recess and partially occluding entry therein of the mount, said latch member being deflectable relative said carrier tube by movement of said mount into said recess translationally along its extension axis aligned with the tube connection axis so as to bias the latch member between said carrier tube and said mount in contacting relationship with said outwardly directed surfaces of said mount to frictionally engage said brush section on said mount, and wherein the latch member is configured as a sleeve received within the carrier tube.

26. A replaceable brush section for an electrical toothbrush having a hand piece and an output drive shaft movably disposed therein, said hand piece having a mount for receiving said brush section, said mount extending from the hand piece along an extension axis, and said output drive shaft being movable with respect to said mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles, the bristle carrier being rotatable relative the carrier tube, said carrier tube having a base region adapted to be removably and fixedly attached to the mount of the toothbrush hand piece by movement of said carrier tube along a tube connection axis toward said mount, said base region being at least partially defined by radially directed lateral surfaces and longitudinally extending along said tube connection axis, said base region radially directed lateral surfaces mating in confronting relationship with opposing said radially directed lateral surfaces of said mount, wherein the base region of the carrier tube has, as seen in a plane transverse to the tube connection axis, a cross-sectional shape not rotationally symmetric about the tube connection axis and adapted to cooperate with said first shape of said brush section-receiving portion of the mount thereby permitting the brush section base region to be attached to the mount at only a certain angular orientation about the extension axis, a longitudinal axle displaceably disposed within the carrier tube, said axle disposed parallel the connection axis and drivingly connected to the bristle carrier and adapted to be coupled to the hand piece output drive shaft during translational movement of the mount into mating relationship with the base region along the connection axis, and at least one resilient member attached to said brush section and formed along a portion of said radially directed lateral surfaces of said base region and having a transverse extent transverse the carrier tube connection axis, said resilient member being deflectable relative said carrier tube by movement of said mount towards mating relationship with said base region translationally along the mount extension axis aligned with the tube connection axis, wherein the resilient member is arranged between at least one said radially directed surface of said base region and at least one said confronting radially directed surface of said mount so that in a deflected condition of loading on the resilient member, the resilient member bears against said mount surface to secure the carrier tube from inadvertent motion relative the mount during operation of the toothbrush, whereby a force tending to pull the brush section in a direction away from the mount is hindered by the resilient member.

27. The brush section of claim 26, wherein the resilient member is disposed on a wall of the carrier tube.

28. The brush section of claim 26, wherein the resilient member is deflectable relative an outerwall surface of the carrier tube.

29. The brush section of claim 26, wherein the resilient member is deflectable relative an innerwall surface of the carrier tube.

30. The brush section of claim 26 in combination with an electric toothbrush hand piece.

31. The brush section of claim 26, wherein said resilient member is elongate.

32. The brush section of claim 26, wherein said resilient member has camming structure facing in a direction at least partially away from the bristle carrier and that is shaped and positioned to interact with corresponding mount structure to facilitate deflection of said resilient member.

33. The brush section of claim 26, wherein the at least one resilient member comprises at least two resilient members located on respective radially inwardly directed surfaces.

34. The brush section of claim 26, wherein the resilient member is defined adjacent a region of a reduced wall thickness formed in the carrier tube.

35. The brush section of claim 26, wherein the resilient member is defined by a localized region of a wall of the brush section having a thickness differing from a wall thickness of a remaining portion of the brush section more remote from the resilient member.

36. The brush section of claim 35, wherein the differing wall thickness is a reduced thickness.

37. The brush section of claim 26, wherein the resilient member is integrally molded with the carrier tube.

38. The brush section of claim 26, wherein the resilient member has a radially directed free surface defining a distributed area contact face adapted to make distributed area contact generally parallel the longitudinal axle with a generally smooth surface of the radially directed lateral surface of the mount.

39. The brush section of claim 26, wherein said longitudinal axle is rotationally disposed within the carrier tube.

40. The brush section of claim 26, wherein the brush section longitudinal axle is disposed for oscillatory rotational motion within the carrier tube to effect oscillatory rotational motion of said bristle carrier.

41. The brush section of claim 26, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

42. The brush section of claim 26, wherein said carrier tube is adapted to receive the output drive shaft, said output shaft extending outwards from said hand piece and protruding therefrom.

43. The brush section of claim 26, wherein said carrier tube radially surrounds said mount when attached thereto.

44. The brush section of claim 26, wherein said carrier tube is made of a plastics material.

45. The brush section of claim 26, wherein said longitudinal axle is adapted to be coupled to the hand piece output drive shaft, said longitudinal axle being rotatable relative the carrier tube and the hand piece mount.

46. The brush section of claim 26, wherein said base region radially directed lateral surfaces are inwardly directed, and said corresponding radially directed lateral surfaces of said mount are outwardly directed.

47. The brush section of claim 26, wherein said carrier tube defines a tube peripheral end face which is axially directed and located most remote from a bristle carrier end of the tube, said base region being adjacent and inward of said end face in a direction extending towards the bristle carrier, said longitudinal axle has a coupling end remote from the bristle carrier, said coupling end being disposed, in an axial direction, inward of the tube peripheral end face, and said resilient member is spaced, in an axial direction, inward of the tube peripheral end face, said resilient member comprising an elastic material.

48. The brush section of claim 26, wherein said resilient member extends longitudinally parallel the carrier tube connection axis.

49. A replaceable brush section for an electrical toothbrush having a hand piece and an output drive shaft movably disposed therein, said hand piece having a mount for receiving said brush section, said mount extending from the hand piece along an extension axis, and said output drive shaft being movable with respect to said mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles, the bristle carrier being rotatable relative the carrier tube, said carrier tube having a base region adapted to be removably and fixedly attached to the mount of the toothbrush hand piece by movement of said carrier tube along a tube connection axis toward said mount, said base region being at least partially defined by radially directed lateral surfaces and longitudinally extending along said tube connection axis, said base region radially directed lateral surfaces mating in confronting relationship with opposing said radially directed lateral surfaces of said mount, wherein the base region of the carrier tube has, as seen in a plane transverse to the tube connection axis, a cross-sectional shape not rotationally symmetric about the tube connection axis and adapted to cooperate with said first shape of said brush section-receiving portion of the mount thereby permitting the brush section base region to be attached to the mount at only a certain angular orientation about the extension axis, a longitudinal axle displaceably disposed within the carrier tube, said axle disposed parallel the connection axis and drivingly connected to the bristle carrier and adapted to be coupled to the hand piece output drive shaft during translational movement of the mount into mating relationship with the base region along the connection axis, and at least one resilient member formed along a portion of said radially directed lateral surfaces of said base region and having a transverse extent transverse the carrier tube connection axis, said resilient member being deflectable relative said carrier tube by movement of said mount towards mating relationship with said base region translationally along the mount extension axis aligned with the tube connection axis, wherein the resilient member is arranged between at least one said radially directed surface of said base region and at least one said confronting radially directed surface of said mount so that in a deflected condition of loading on the resilient member, the resilient member bears against said mount surface to secure the carrier tube from inadvertent motion relative the mount during operation of the toothbrush, whereby a force tending to pull the brush section in a direction away from the mount is hindered by the resilient member, and further comprising a sleeve on which is disposed the at least one resilient member, said sleeve adapted to be inserted onto the carrier tube.

50. The brush section of claim 49, wherein at least one of the sleeve and the carrier tube comprises at least one shoulder forming said at least one resilient member, said at least one shoulder having a camming surface extending in the direction of the mount.

51. The brush section of claim 49, wherein said sleeve is made of a plastics material.

52. The brush section of claim 51, wherein said resilient member is molded integrally with the sleeve.

53. The brush section of claim 51, wherein the resilient member is made of elastic material molded with the sleeve.

54. The brush section of claim 49, wherein the resilient member is defined adjacent a region of a reduced wall thickness formed in the sleeve.

55. A replaceable brush section for an electrical toothbrush having a hand piece and an output drive shaft movably disposed therein, said hand piece having a mount for receiving said brush section, said mount extending from the hand piece along an extension axis, and said output drive shaft being movable with respect to said mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles, the bristle carrier being rotatable relative the carrier tube, said carrier tube having a base region adapted to be removably and fixedly attached to the mount of the toothbrush hand piece by movement of said carrier tube along a tube connection axis toward said mount, said base region being at least partially defined by radially directed lateral surfaces and longitudinally extending along said tube connection axis, said base region radially directed lateral surfaces mating in confronting relationship with opposing said radially directed lateral surfaces of said mount, wherein the base region of the carrier tube has, as seen in a plane transverse to the tube connection axis, a cross-sectional shape not rotationally symmetric about the tube connection axis and adapted to cooperate with said first shape of said brush section-receiving portion of the mount thereby permitting the brush section base region to be attached to the mount at only a certain angular orientation about the extension axis, a longitudinal axle displaceably disposed within the carrier tube, said axle disposed parallel the connection axis and drivingly connected to the bristle carrier and adapted to be coupled to the hand piece output drive shaft during translational movement of the mount into mating relationship with the base region along the connection axis, and at least one resilient member formed along a portion of said radially directed lateral surfaces of said base region and having a transverse extent transverse the carrier tube connection axis, said resilient member being deflectable relative said carrier tube by movement of said mount towards mating relationship with said base region translationally along the mount extension axis aligned with the tube connection axis, wherein the resilient member is arranged between at least one said radially directed surface of said base region and at least one said confronting radially directed surface of said mount so that in a deflected condition of loading on the resilient member, the resilient member bears against said mount surface to secure the carrier tube from inadvertent motion relative the mount during operation of the toothbrush, whereby a force tending to pull the brush section in a direction away from the mount is hindered by the resilient member, and wherein the resilient member is constructed as a cantilever beam member.

56. The brush section of claim 55, wherein the cantilever beam member is defined between two slots formed in the brush section one on either side of the beam.

57. The brush section of claim 55, wherein said resilient cantilever beam has camming structure facing in a direction at least partially away from the bristle carrier and that is shaped and positioned to interact with corresponding mount structure to facilitate deflection of said cantilever beam.

58. A replaceable brush section for an electrical toothbrush having a hand piece and an output drive shaft movably disposed therein, said hand piece having a mount for receiving said brush section, said mount extending from the hand piece along an extension axis, and said output drive shaft being movable with respect to said mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles, the bristle carrier being rotatable relative the carrier tube, said carrier tube having a base region adapted to be removably and fixedly attached to the mount of the toothbrush hand piece by movement of said carrier tube along a tube connection axis toward said mount, said base region being at least partially defined by radially directed lateral surfaces and longitudinally extending along said tube connection axis, said base region radially directed lateral surfaces mating in confronting relationship with opposing said radially directed lateral surfaces of said mount, wherein the base region of the carrier tube has, as seen in a plane transverse to the tube connection axis, a cross-sectional shape not rotationally symmetric about the tube connection axis and adapted to cooperate with said first shape of said brush section-receiving portion of the mount thereby permitting the brush section base region to be attached to the mount at only a certain angular orientation about the extension axis, a longitudinal axle displaceably disposed within the carrier tube, said axle disposed parallel the connection axis and drivingly connected to the bristle carrier and adapted to be coupled to the hand piece output drive shaft during translational movement of the mount into mating relationship with the base region along the connection axis, and at least one resilient member formed along a portion of said radially directed lateral surfaces of said base region and having a transverse extent transverse the carrier tube connection axis, said resilient member being deflectable relative said carrier tube by movement of said mount towards mating relationship with said base region translationally along the mount extension axis aligned with the tube connection axis, wherein the resilient member is arranged between at least one said radially directed surface of said base region and at least one said confronting radially directed surface of said mount so that in a deflected condition of loading on the resilient member, the resilient member bears against said mount surface to secure the carrier tube from inadvertent motion relative the mount during operation of the toothbrush, whereby a force tending to pull the brush section in a direction away from the mount is hindered by the resilient member, and wherein the resilient member is configured as a sleeve received within the carrier tube.

59. A brush section for an electric toothbrush hand piece having a rotary drive shaft and a mount adapted to receive said brush section, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles, said bristle carrier rotatable relative the carrier tube, a longitudinal axle rotationally disposed within the carrier tube and drivingly connected to the bristle carrier and adapted to be coupled to the rotary drive shaft of the hand piece, said carrier tube having a base region adapted to plug onto the mount of the hand piece, wherein at least one spring element is fitted to the brush section and is flexible within the brush section and is arranged between a radially inwardly directed surface of the carrier tube and a confronting radially outwardly directed surface of the mount, and wherein the base region of the carrier tube has, as seen in a plane transverse to the longitudinal axle, a cross-sectional shape not rotationally symmetric about the longitudinal axle and adapted to cooperate with said first shape of said brush section-receiving portion of the mount whereby the plugged-on carrier tube is non-rotatable relative the mount.

60. The brush section of claim 59, wherein the at least one spring element is deflectable relative the carrier tube upon plugging the brush section onto the mount.

61. The brush section of claim 59, wherein the at least one spring element is disposed on the carrier tube.

62. The brush section of claim 59 in combination with an electric toothbrush hand piece.

63. The brush section of claim 59, wherein the carrier tube is adapted to surround the mount in a radial direction.

64. The brush section of claim 59, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

65. The brush section of claim 59, wherein the brush section longitudinal axle is disposed for oscillatory rotational motion within the carrier tube to effect oscillatory rotational motion of said bristle carrier.

66. A brush section for an electric toothbrush hand piece having a rotary drive shaft, said brush section comprising a carrier tube to which is fitted a bristle carrier comprising a plurality of bristles, said bristle carrier rotatable relative the carrier tube, a longitudinal axle rotationally disposed within the carrier tube and drivingly connected to the bristle carrier and adapted to be coupled to the rotary drive shaft of the hand piece, and said carrier tube being adapted to plug onto a mount of the hand piece of the electric toothbrush, wherein at least one spring element is fitted to the brush section and is flexible within the brush section and is arranged between a radially inwardly directed surface of the carrier tube and a confronting radially outwardly directed surface of the mount and the plugged-on carrier tube is non-rotatable relative the mount, and further comprising a sleeve on which is disposed the at least one spring element, said sleeve being adapted to plug into the carrier tube.

67. The brush section of claim 66, wherein at least one of the sleeve and the carrier tube comprises at least one shoulder forming said at least one spring element, said at least one shoulder having a bend extending in the direction of the mount.

68. The brush section of claim 66, wherein at least one of the sleeve and the carrier tube comprises a plastics material.

69. The brush section of claim 66, wherein the at least one spring element is made of elastic material molded with the sleeve.

70. The brush section of claim 66, wherein the at least one spring element is deflectable relative the carrier tube upon plugging the brush section onto the mount.

71. A brush section for an electric toothbrush hand piece having a rotary drive shaft, said brush section comprising a carrier tube to which is fitted a bristle carrier comprising a plurality of bristles, said bristle carrier rotatable relative the carrier tube, a longitudinal axle rotationally disposed within the carrier tube and drivingly connected to the bristle carrier and adapted to be coupled to the rotary drive shaft of the hand piece, and said carrier tube being adapted to plug onto a mount of the hand piece of the electric toothbrush, wherein at least one spring element is fitted to the brush section and is flexible within the brush section and is arranged between a radially inwardly directed surface of the carrier tube and a confronting radially outwardly directed surface of the mount and the plugged-on carrier tube is non-rotatable relative the mount, and wherein the at least one spring element is configured as a cantilever beam member.

72. A brush section for an electric toothbrush hand piece having a rotary drive shaft, said brush section comprising a carrier tube to which is fitted a bristle carrier comprising a plurality of bristles, said bristle carrier rotatable relative the carrier tube, a longitudinal axle rotationally disposed within the carrier tube and drivingly connected to the bristle carrier and adapted to be coupled to the rotary drive shaft of the hand piece, and said carrier tube being adapted to plug onto a mount of the hand piece of the electric toothbrush, wherein at least one spring element is fitted to the brush section and is flexible within the brush section and is arranged between a radially inwardly directed surface of the carrier tube and a confronting radially outwardly directed surface of the mount and the plugged-on carrier tube is non-rotatable relative the mount, and wherein the at least one spring element is configured as a sleeve received within the carrier tube.

73. A brush section for an electric toothbrush hand piece having a housing defining a mount that is stationary in operation relative the housing and an output drive shaft that moves relative the mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles and having a base region adapted to plug onto the mount of the hand piece of the electric toothbrush such that said carrier tube is stationary in operation relative the housing, said bristle carrier being movable relative the carrier tube, and further comprising a longitudinal axle movably disposed within the carrier tube and drivingly connected to the bristle carrier and adapted to be coupled to the hand piece output drive shaft, wherein at least one spring element is arranged between a radially inwardly directed surface of the carrier tube and a confronting radially outwardly directed surface of the mount and is flexibly attached to the brush section to thus frictionally engage the carrier tube to the mount inhibiting relative movement therebetween during operation of the toothbrush, and wherein the base region of the carrier tube has, as seen in a plane transverse to the longitudinal axle, a cross-sectional shape not rotationally symmetric about the longitudinal axle and adapted to cooperate with said first shape of said brush section-receiving portion of the mount whereby the plugged-on carrier tube is non-rotatable relative the mount.

74. The brush section of claim 73, wherein the at least one spring element is disposed on the carrier tube.

75. The brush section of claims 73, wherein the at least one spring element is deflectable relative the carrier tube upon plugging the brush section onto the mount.

76. The brush section of claim 73, wherein the at least one spring element is configured as a cantilever beam.

77. The brush section of claim 73 in combination with an electric toothbrush hand piece.

78. The brush section of claim 73, wherein the at least one spring element is attached to said brush section.

79. The brush section of claim 73, wherein the carrier tube is adapted to surround the mount in a radial direction.

80. The brush section of claim 73, wherein a brush section longitudinal axle is disposed for oscillatory rotational motion within the carrier tube to effect oscillatory rotational motion of said bristle carrier.

81. The brush section of claim 73, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

82. A brush section for an electric toothbrush hand piece having a housing defining a mount that is stationary in operation relative the housing, said brush section comprising a carrier tube to which is fitted a bristle carrier comprising a plurality of bristles and being adapted to plug onto the mount of the hand piece of the electric toothbrush such that said carrier tube is stationary in operation relative the housing, and wherein at least one spring element is arranged between a radially inwardly directed surface of the carrier tube and a confronting radially outwardly directed surface of the mount and is flexibly attached to the brush section to thus frictionally engage the carrier tube to the mount inhibiting relative movement therebetween during operation of the toothbrush and the plugged-on carrier tube is non-rotatable relative the mount, and further comprising a sleeve on which is disposed the at least one spring element, said sleeve being adapted to plug into the carrier tube.

83. The brush section of claim 82, wherein the resilient element is made of elastic material molded with the sleeve.

84. The brush section of claim 82, wherein at least one of the sleeve and the carrier tube comprises at least one shoulder forming said at least one spring element, said at least one shoulder having a bend extending in the direction of the mount.

85. The brush section of claim 82, wherein at least one of the sleeve and the carrier tube comprises a plastics material.

86. A brush section for an electric toothbrush hand piece having a housing defining a mount that is stationary in operation relative the housing, said brush section comprising a carrier tube to which is fitted a bristle carrier comprising a plurality of bristles and being adapted to plug onto the mount of the hand piece of the electric toothbrush such that said carrier tube is stationary in operation relative the housing, and wherein at least one spring element is arranged between a radially inwardly directed surface of the carrier tube and a confronting radially outwardly directed surface of the mount and is flexibly attached to the brush section to thus frictionally engage the carrier tube to the mount inhibiting relative movement therebetween during operation of the toothbrush and the plugged-on carrier tube is non-rotatable relative the mount, and wherein the at least one spring element is configured as a sleeve received within the carrier tube.

87. A brush section for an electric toothbrush hand piece having a mount and an output drive shaft extending through said mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles and said carrier tube having a base region adapted to plug onto the mount of the hand piece, said carrier tube having a longitudinally extending tube connection axis, wherein at least one spring element is attached to the brush section and is arranged between a radially inwardly directed surface of the carrier tube and a confronting radially outwardly directed surface of the mount and bears against the mount inhibiting a driving motion of the extending end of the output drive shaft which causes bristle carrier rotation from causing motion of the carrier tube, and wherein the base region of the carrier tube has, as seen in a plane transverse to the tube connection axis, a cross-sectional shape not rotationally symmetric about the tube connection axis and adapted to cooperate with said first shape of said brush section-receiving portion of the mount whereby the plugged-on carrier tube is non-rotatable relative the mount.

88. The brush section of claim 87, wherein the at least one spring is flexibly attached to the brush section.

89. The brush section of claim 87, wherein the at least one spring element is deflectable relative the carrier tube upon plugging the brush section onto the mount.

90. The brush section of claim 87, wherein the at least one spring element is disposed on the carrier tube.

91. The brush section of claim 87 in combination with an electric toothbrush hand piece.

92. The brush section of claim 87, wherein the carrier tube is adapted to surround the mount in a radial direction.

93. The brush section of claim 87, wherein the brush section longitudinal axle is disposed for oscillatory rotational motion within the carrier tube to effect oscillatory rotational motion of said bristle carrier.

94. The brush section of claim 87, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

95. A brush section for an electric toothbrush hand piece having a mount and an output drive shaft extending through said mount, said brush section comprising a carrier tube to which is fitted a bristle carrier comprising a plurality of bristles and being adapted to plug onto the mount of the hand piece, wherein at least one spring element is attached to the brush section and is arranged between a radially inwardly directed surface of the carrier tube and a confronting radially outwardly directed surface of the mount and bears against the mount inhibiting a driving motion of the extending end of the output drive shaft which causes bristle carrier rotation from causing motion of the carrier tube and the plugged-on carrier tube is non-rotatable relative the mount, and further comprising a sleeve on which is disposed the at least one spring element, said sleeve being adapted to plug into the carrier tube.

96. The brush section of claim 95, wherein the at least one spring is made of elastic material molded with the sleeve.

97. The brush section of claim 95, wherein at least one of the sleeve and the carrier tube comprises at least one shoulder forming said at least one spring element, said at least one shoulder having a bend extending in the direction of the mount.

98. The brush section of claim 95, wherein at least one of the sleeve and the carrier tube comprises a plastics material.

99. A brush section for an electric toothbrush hand piece having a mount and an output drive shaft extending through said mount, said brush section comprising a carrier tube to which is fitted a bristle carrier comprising a plurality of bristles and being adapted to plug onto the mount of the hand piece, wherein at least one spring element is attached to the brush section and is arranged between a radially inwardly directed surface of the carrier tube and a confronting radially outwardly directed surface of the mount and bears against the mount inhibiting a driving motion of the extending end of the output drive shaft which causes bristle carrier rotation from causing motion of the carrier tube and the plugged-on carrier tube is non-rotatable relative the mount, and wherein the at least one spring element is configured as a sleeve received within the carrier tube.

100. A brush section for an electric toothbrush having a hand piece defining a mount for receiving said brush section and having an output drive shaft, said mount extending from the hand piece along an extension axis, and said output drive shaft being movable with respect to said mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles and having a base region adapted to removably and fixedly plug onto the mount of the hand piece, said bristle carrier being movable relative the carrier tube, and further comprising a longitudinal axle movably disposed within the carrier tube and drivingly connected to the bristle carrier and adapted to be coupled to the hand piece output drive shaft, the base region having inwardly directed side surfaces for mating with outwardly directed surfaces of the mount, wherein the inwardly directed surfaces of the brush section tube have, as seen in a plane transverse to the longitudinal axle, a cross-sectional shape not rotationally symmetric about the longitudinal axle and adapted to cooperate with said first shape of said brush section-receiving portion of the mount to attach said brush section to said mount at a predetermined angular orientation about the extension axis, and wherein at least one spring element is attached to the brush section and is arranged between a radially inwardly directed surface of the carrier tube and a confronting radially outwardly directed surface of the mount and frictionally engages the carrier tube to the mount inhibiting relative movement therebetween during operation of the toothbrush.

101. The brush section of claim 100, wherein the at least one spring element is deflectable relative the carrier tube upon plugging the brush section onto the mount.

102. The brush section of claim 100, wherein the at least one spring element is disposed on the carrier tube.

103. The brush section of claim 100, wherein the at least one spring element is provided on at least one of the hand piece and the mount.

104. The brush section of claim 100 in combination with an electric toothbrush hand piece.

105. The brush section of claim 100, wherein the at least one spring element is attached to said brush section.

106. The brush section of claim 100, wherein the carrier tube is adapted to surround the mount in a radial direction.

107. The brush section of claim 100, wherein the brush section further comprises a longitudinal axle disposed for oscillatory rotational motion within the carrier tube and drivingly connected to the bristle carrier to effect oscillatory rotational motion of said bristle carrier.

108. The brush section of claim 100, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

109. A brush section for an electric toothbrush having a hand piece defining a mount for receiving said brush section and having an output drive shaft, said mount extending from the hand piece along an extension axis, and said output drive shaft being movable with respect to said mount, said mount having a brush section-receiving portion at least partially defined by radially directed lateral surfaces of said mount, said brush-section receiving portion having in cross-section a first shape, said brush section comprising a carrier tube to which is fitted a bristle carrier comprising a plurality of bristles and having a base region adapted to removably and fixedly plug onto the mount of the hand piece, said carrier tube having a longitudinally extending tube connection axis, the base region having inwardly directed side surfaces for mating with outwardly directed surfaces of the mount, wherein the inwardly directed surfaces of the brush section tube have, as seen in a plane transverse to the tube connection axis, a cross-sectional shape not rotationally symmetric about the tube connection axis and adapted to cooperate with said first shape of said brush section-receiving portion of the mount to attach said brush section to said mount at a predetermined angular orientation about the extension axis, wherein at least one spring element is attached to the brush section and is arranged between a radially inwardly directed surface of the carrier tube and a confronting radially outwardly directed surface of the mount and frictionally engages the carrier tube to the mount inhibiting relative movement therebetween during operation of the toothbrush, and further comprising a sleeve on which is disposed the at least one spring element, said sleeve being adapted to plug into the carrier tube.

110. The brush section of claim 109, wherein at least one of the sleeve and the carrier tube comprises at least one shoulder forming said at least one spring element, said at least one shoulder having a bend extending in the direction of the mount.

111. The brush section of claim 109, wherein at least one of the sleeve and the carrier tube comprises a plastics material.

112. A brush section for an electric toothbrush hand piece having a housing defining a mount having a radially outwardly directed surface and an output drive shaft extending from the hand piece and being moveable with respect to the mount, said brush section comprising a carrier tube to which is fitted a bristle carrier comprising a plurality of bristles and being adapted to plug onto the mount of the hand piece, said bristle carrier being movable relative the carrier tube, wherein at least one resilient spring element is attached to the brush section and is arranged between a radially inwardly directed surface of the carrier tube and the confronting radially outwardly directed surface of the mount and frictionally engages the carrier tube to the mount inhibiting relative movement therebetween during operation of the toothbrush, and the inwardly directed surface of the carrier tube is rotationally asymmetric such that the plugged-on carrier tube is non-rotatable relative the mount.

113. The brush section of claim 112, wherein the spring element resiliently latches the carrier tube to the mount.

114. The brush section of claim 112, wherein the spring element is constructed as a cantilever beam.

115. The brush section of claim 112, wherein the spring element is made of a plastics material.

116. The brush section of claim 112, wherein the at least one spring element is disposed on a wall of the carrier tube.

117. The brush section of claim 112 in combination with an electric toothbrush hand piece.

118. The brush section of claim 112, wherein the at least one spring element is attached to said brush section.

119. The brush section of claim 112, wherein the drive shaft extends through the mount and the carrier tube is adapted to surround the mount in a radial direction.

120. The brush section of claim 112, wherein the bristle carrier is rotatable relative the carrier tube, and further comprising a longitudinal axle rotationally disposed within the carrier tube and drivingly connected to the bristle carrier and adapted to be coupled to the hand piece output drive shaft when the carrier tube is plugged onto the mount.

121. The brush section of claim 120, wherein the brush section longitudinal axle is disposed for oscillatory rotational motion within the carrier tube to effect oscillatory rotational motion of said bristle carrier.

122. The brush section of claim 112, wherein the spring element has a radially inwardly directed free surface defining a distributed area contact face adapted to make distributed area contact, generally parallel a longitudinal axis of the carrier tube, with a generally smooth surface of the radially outwardly directed lateral surface of the mount.

123. The brush section of claim 112, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

124. The brush section of claim 112, wherein the carrier tube has a longitudinally extending tube connection axis and the inwardly directed surfaces of the brush section have, as seen in a plane transverse to the tube connection axis, a cross-sectional shape not rotationally symmetric about the tube connection axis to thereby cooperate with the outwardly directed surfaces to attach said brush section to said mount at a predetermined orientation.

* * * * *